(12) United States Patent
Hwang et al.

(10) Patent No.: US 7,384,872 B2
(45) Date of Patent: Jun. 10, 2008

(54) METHOD OF PRODUCING SUBSTRATE HAVING PATTERNED ORGANOSILANE LAYER AND METHOD OF USING THE SUBSTRATE HAVING THE PATTERNED ORGANOSILANE LAYER

(75) Inventors: Kyu-youn Hwang, Incheon (KR); Ji-na Namgoong, Gyeonggi-do (KR); Jeo-young Shim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 63 days.

(21) Appl. No.: 11/130,756

(22) Filed: May 17, 2005

(65) Prior Publication Data

US 2005/0272268 A1   Dec. 8, 2005

(30) Foreign Application Priority Data

Jun. 2, 2004   (KR) ...................... 10-2004-0039983

(51) Int. Cl.
*H01L 21/311* (2006.01)
(52) U.S. Cl. ...................... 438/694; 438/689; 438/778; 438/780
(58) Field of Classification Search ................ 438/689, 438/694, 778, 780; 436/527, 528
See application file for complete search history.

(56) References Cited

U.S. PATENT DOCUMENTS

| 4,330,569 | A | * | 5/1982 | Gulett et al. ................. | 427/539 |
|---|---|---|---|---|---|
| 5,688,642 | A | * | 11/1997 | Chrisey et al. ................. | 435/6 |
| 6,193,352 | B1 | * | 2/2001 | Sharma et al. ................. | 347/28 |
| 6,881,379 | B1 | * | 4/2005 | Bredehorst et al. ........... | 422/58 |
| 7,160,687 | B1 | * | 1/2007 | Kapur et al. ................. | 435/7.2 |
| 2002/0034923 | A1 | * | 3/2002 | Bookbinder et al. .......... | 451/37 |
| 2007/0190656 | A1 | * | 8/2007 | Crain et al. .................... | 436/63 |

FOREIGN PATENT DOCUMENTS

JP          64000902 A   *   1/1989

OTHER PUBLICATIONS

Sapsford et al. (Journal of applied Microbiology 2004, 96,pp. 47-58)☐☐.*
Ji-Yen Cheng et al. (Sensors and Actuators, B 99 (2004) 186-196).*

* cited by examiner

*Primary Examiner*—Nadine Norton
*Assistant Examiner*—Mahmoud Dahimene
(74) *Attorney, Agent, or Firm*—Cantor Colburn LLP

(57) ABSTRACT

Provided are a method of producing a substrate having a patterned organosilane layer and a method of using the substrate having the patterned organosilane layer. The method of producing the substrate having the patterned organosilane layer, includes: coating organosilane on a substrate to obtain an organosilane layer; coating a photoresist material on the organosilane layer; exposing the photoresist material to light through a mask to obtain a patterned surface on the photoresist material; developing an exposed or unexposed region of the photoresist material using a developer; and wet etching a portion of the organosilane layer in the region from which the photoresist material has been removed, using a HF-containing solution as an etchant.

8 Claims, 5 Drawing Sheets

(A)

(B)

AUTOFLUORESCENCE

Au/Ag STAINING

FITC STAINING

AUTOFLUORESCENCE

Au/Ag STAINING

FITC STAINING (A) (B)

SEQUENCE LISTING

<160> NUMBER OF SEQ ID NOS: 2

<210> SEQ ID NO 1
<211> LENGTH: 15
<212> TYPE: DNA
<213> ORGANISM: Artificial
<220> FEATURE:
<223> OTHER INFORMATION: oligonucleotide immoblized on the patterned
      substrate : 5' termianl is modified with NH2-(CH2)6- group

<400> SEQUENCE: 1
cggaggaacc gtttc                                                    15

<210> SEQ ID NO 2
<211> LENGTH: 15
<212> TYPE: DNA
<213> ORGANISM: Artificial
<220> FEATURE:
<223> OTHER INFORMATION: target oligonucleotide : 3' terminal is
      labelled with Cy-3

<400> SEQUENCE: 2
gcctccttgg caaag                                                    15

US 7,384,872 B2

METHOD OF PRODUCING SUBSTRATE HAVING PATTERNED ORGANOSILANE LAYER AND METHOD OF USING THE SUBSTRATE HAVING THE PATTERNED ORGANOSILANE LAYER

BACKGROUND OF THE INVENTION

This application claims the benefit of Korean Patent Application No. 10-2004-0039983, filed on Jun. 2, 2004, in the Korean Intellectual Property Office, the disclosure of which is incorporated herein in its entirety by reference.

1. Field of the Invention

The present invention relates to a method of producing a substrate having a patterned organosilane layer and a method of using the substrate having the patterned organosilane layer.

2. Description of the Related Art

A method of patterning a thin organosilane layer comprising a self-assembled monolayer is known. In general, an organosilane layer is patterned using photolithography. For example, U.S. Pat. No. 5,688,642 describes a method of producing a substrate having a patterned organosilane layer. In the method, a substrate having a hydroxyl group is coated with organosilane, exposed to UV light (193 nm) using a lithographic mask and etched the exposed portion. The etching of the organosilane layer is performed by dry etching. That is, the organosilane layer is selectively exposed to the UV light for a long time and the exposed layer is selectively removed. However, such a dry etching requires considerable time and can be applied only to an organosilane compound which is reactive to UV light having a specific wavelength.

U.S. Pat. No. 5,474,796 describes a method of producing an array plate using photolithography. First, a photoresist is coated on a substrate and exposed to light and developed to form a patterned region composed of a first exposed surface and a surface coated with the photoresist. Then, the first exposed surface is reacted with fluoroalkylsilane to form a stable hydrophobic fluoroalkylsiloxane matrix on the first exposed surface. Next, the photoresist layer is removed to form a second exposed surface. Then, the second exposed surface is reacted with a hydroxy or aminoakylsilane group so as to convert the second exposed surface to a hydrophilic binding region. Thus, the substrate has the hydrophilic binding region composed of the hydroxy or aminoakylsilane group and the hydrophobic non-binding region composed of fluoroalkylsiloxane. In this method, the pattern is formed by selectively removing the photoresist and directly etching the organosilane layer.

In the conventional methods described above, the thin organosilane layer comprising the self assembled monolayer is directly patterned using the dry etching or, without directly forming a pattern on the organosilane layer, the photoresist is selectively removed to form a pattern and then, selectively reacted with the organosilane layer to obtain a pattern. Thus, a method in which a thin organosilane layer is directly patterned using a wet etching has not been reported. The present inventors conducted research on a method of wet etching a thin organosilane layer which can be performed in a quicker and simpler manner and in larger scale compared to the dry etching method and discovered that an organosilane layer may be etched using a HF-containing solution.

SUMMARY OF THE INVENTION

The present invention provides a method of producing a substrate having a patterned organosilane layer using wet etching.

The present invention also provides a method of producing a biomolecule microarray using the substrate having the patterned organosilane layer.

According to an aspect of the present invention, there is provided a method of producing a substrate having a patterned organosilane layer, comprising:

coating organosilane on a substrate to obtain an organosilane layer;

coating a photoresist material on the organosilane layer;

exposing the photoresist material to light through a mask to obtain a patterned surface on the photoresist material;

developing an exposed or unexposed region of the photoresist material using a developer; and wet etching a portion of the organosilane layer in the region from which the photoresist material has been removed, using a HF-containing solution as an etchant.

According to another aspect of the present invention, there is provided a method of using the substrate having the patterned organosilane layer produced using the above method, comprising:

reacting the patterned surface of the substrate with a substance.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
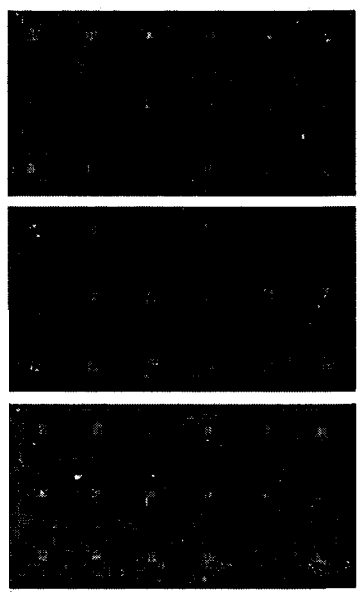
FIG. 1 illustrates the results of the fluorescent measurements at 532 nm for autofluorescence signals and signals after staining with gold/silver or FITC of substrates having a patterned organosilane layer produced using a method according to an embodiment of the present invention, observed using a scanner.
Figure 1:

According to an embodiment of the present invention, there is provided a method of producing a substrate having a patterned organosilane layer, comprising:

coating organosilane on a substrate to obtain an organosilane layer;

coating a photoresist material on the organosilane layer;

exposing the photoresist material to light through a mask to obtain a patterned surface on the photoresist material;

developing an exposed or unexposed region of the photoresist material using a developer; and wet etching a portion of the organosilane layer in the region from which the photoresist material has been removed, using a HF-containing solution as an etchant.

First, in the method according to an embodiment of the present invention, organosilane is coated on the substrate to obtain the organosilane layer. A coating method of organosilane on a substrate is well known in the art. Various methods used in coating a thin film on a silicon wafer during manufacturing a semiconductor device, for example, spin coating, dip coating, and chemical vapor deposition, can be used. The organosilane layer may be a self-assembled monolayer or bilayer. Any organosilane which has at least one alkoxy group on a silicon atom can be used. The organosilane may be selected from the group consisting of aminosilane, epoxysilane, and fluorosilane. Examples of the aminosilane include, but are not limited to, γ-aminopropyltriethoxysilane (GAPS) and N-(2-aminoethyl)-3-aminopropyltrimethoxysilane. Examples of the epoxysilane include, but are not limited to, (3-glycidoxypropy)trimethoxysilane and 2-(3,4-epoxycyclohexyl)ethyltrimethoxysilane. Examples of the fluorosilane include, but are not limited to, 1H,1H,2H,2H-perfluorodecyltriethoxysilane and triethoxyfluorosilane.

The organosilane used according to an embodiment of the present invention may have a suitable functional group according to the type of a biomolecule to be immobilized on the substrate produced using the method. When a polynucleotide is to be immobilized on the substrate, the organosilane having an amino group on its end may be used. Examples of a terminal functional group which can be contained in the organosilane include thiol, olefine, acetal, epoxy, and benzyl halide groups. The biomolecule may be bound to the functional group via a crosslinker, thereby immobilizing the biomolecule on the substrate.

In the coating of the organosilane on the substrate, it may be any substrate to which the organosilane can be coated. The substrate may be modified to have a hydroxyl group, which can be bound to the organosilane, on its surface. Examples of a substrate material include, but are not limited to, inorganic materials, such as silicon, glass, silica, diamond, quartz, alumina, silicon nitride, platinum, gold, aluminum, tungsten, titanium, various other metals, and various other ceramic materials, or organic materials such as polymers, such as polyester, polyamide, polyimide, acrylics, polyether, polysulfone, and fluoropolymer. The substrate may comprise an oxide layer on its surface. The oxide layer may be made of $SiO_2$, $Al_2O_3$, $TiO_2$, or indium tin oxide (ITO), but not being limited thereto. When the organosilane layer is etched using the HF-containing solution, the oxide layer can be simultaneously etched. Thus, the patterned substrate can be produced in a simple process with low costs. For example, when the organosilane layer is formed on the substrate with a $SiO_2$ coating, the portions of the organosilane layer and the $SiO_2$ layer in the region from which the photoresist material has been removed may be selectively wet etched using the HF-containing solution as the etchant.

In the coating of the photoresist material on the organosilane layer, the photoresist material refers to a material of which solubility in a specific solution, i.e., a developer is changed due to exposure to light. The photoresist material is well known in the art and widely used in a photolithographic process. The photoresist material should be sensitive to a relatively very small amount of light and be able to be removed using the developer. The developer does not remove nor react with the organosilane or substrate layer disposed below the photoresist material layer. Examples of the photoresist material used in an embodiment of the present invention include S-1400-11 ™ (diazonaphtoquinone-type: positive photoresist, manufactured by Shipley) containing an aqueous alkali developer MF312 CD27™ (0.27 M tetramethylammonium hydroxide, manufactured by Shipley), and GXR601 (manufactured by Clariant). Examples of a negative photoresist material include SAL601-ER™ (manufactured by Shipley).

Next, the photoresist material coated on the organosilane layer is exposed to light through the mask to obtain the patterned surface of the photoresist material. Typically, the exposure to light is performed at an UV wavelength, although other wavelengths may be used, especially where differentiation between exposed and unexposed regions of the surface is accomplished with the aid of a photoresist. A wide range of UV light may be used, from deep UV (150-300 nm) to near UV (350-500 nm). A wavelength band of G-line (436 nm) or I-line (365 nm) produced by a mercury lamp is generally used, but not being limited thereto. The pattern is typically generated by exposure through a lithographic mask composed of UV opaque and UV transparent regions in contact with the surface of the photoresist material, but may also be formed using projection printing, direct laser writing, or electron beam lithography. Such processes are well known in the art using a lithographic process, such as semiconductor manufacturing.

The exposed or unexposed region of the photoresist material is developed using the developer. A developing process refers to a process in which an exposed or unexposed region of a photoresist material is dissolved in a developer to remove the exposed or the unexposed region of the photoresist material. When a positive-tone photoresist is used, the exposed region become soluble in the developer, whereas regions which are protected from irradiation by opaque areas of the mask remain largely insoluble when treated with the developer. Conversely, a negative-tone photoresist is soluble only in the unexposed regions. Such a process is well known in the art using a lithographic process, such as semiconductor manufacturing.

The portion of the organosilane layer in the region from which the photoresist material has been removed is etched using the HF-containing solution as an etchant. The HF-containing solution may be an HF solution, a buffered HF solution, or a solution containing HF as a primary component. An etching process refers to a process in which a thin layer, for example, an oxide layer, an organosilane layer, or a substrate layer, which is disposed below a photoresist material layer is selectively removed. In a wet etching process, the thin layer which is disposed below the photoresist material layer is selectively removed using a solution containing chemical substance. By using the HF-containing solution as the etchant, the organosilane layer can be selectively removed regardless of whether the organosilane has a photolytic property or not. The organosilane layer and the thin layer, such as an oxide layer, which is disposed below the organosilane layer can be simultaneously selectively removed, if necessary. Thus, the organosilane layer or the thin layer disposed below the organosilane layer can be selectively removed in a non-specific, simple manner at low costs, compared to the conventional process comprising removing the organosilane layer using light. Further, the wet etching can be performed on a large scale.

In an embodiment of the present invention, the photoresist material can be selectively removed using a stripper. The photoresist material is or is not removed according to the application of the substrate having the patterned organosilane layer, produced using the method according to an embodiment of the present invention. For example, when a functional group is introduced into a portion of the substrate exposed after the etching process in order to immobilize a biomolecule, for example, polynucleotide or protein on the exposed portion, the introduction of the functional group can be performed without removing the remaining photoresist material.

The substrate having the patterned surface produced using the method according to an embodiment of the present invention can be used for production of a microstructure, such as immobilization of a biomolecule and metal plating, but not being limited thereto. The processes of biomolecule immobilization and metal plating on a patterned surface are well known in the art. In the immobilization of the biomolecule, the biomolecule may be immobilized on a portion of an oxide layer or a substrate surface exposed by etching or a selectively exposed organosilane layer. The selectively exposed oxide layer, substrate surface, or organosilane layer may have a functional group which can bind covalently or non-covalently to the biomolecule or may be derivatized to have such a functional group. For example, when a polynucleotide is immobilized on the selectively exposed portion of the organosilane layer, the organosilane layer may have a functional group capable of binding the polynucleotide at its end opposite to the substrate. Examples of the functional group include, but are not limited to, an amino group and an epoxy group. The selectively exposed oxide layer, substrate surface, or organosilane layer may be derivatized with a bifunctional crosslinker to immobilze the biomolecule.

Thus, according to another embodiment of the present invention, there is provided a method of using the substrate having the patterned organosilane layer produced using the above method according to an embodiment of the present invention, comprising: reacting the patterned surface of the substrate with a substance. The substance reacted with the patterned surface of the substrate may be a biomolecule or a metal. Examples of the metal include, but are not limited to, copper, gold, and aluminum. Examples of the biomolecule include, but are not limited to, a nucleic acid, a protein, and a polysaccharide.

According to still another embodiment of the present invention, there is provided a method of producing a biomolecule array, comprising: immobilizing a biomolecule on a patterned surface of the substrate having the patterned organosilane layer produced using the above method according to an embodiment of the present invention.

In this method, the producing of the above substrate having the patterned organosilane layer may comprise: coating organosilane on a substrate to obtain an organosilane layer; coating a photoresist material on the organosilane layer; exposing the photoresist material to light through a mask to obtain a patterned surface on the photoresist material; developing an exposed or unexposed region of the photoresist material using a developer; wet etching a portion of the organosilane layer in the region from which the photoresist material has been removed, using a HF-containing solution as an etchant; and removing a remaining photoresist material.

The organosilane used in an embodiment of the present invention may be aminosilane, epoxysilane, or fluorosilane and the biomolecule may be a polynucleotide, a protein, or polysaccharide. The examples of aminosilane, epoxysilane, or fluorosilane are the same as described in the above.

Further, the process of immobilization is also as the same as described in the above.

Hereinafter, the present invention will be described in more detail with reference to the following examples. However, these examples are given for the purpose of illustration and are not intended to limit the scope of the invention.

EXAMPLES

Example 1

Production of a Silicon Substrate Having a Patterned Aminosilane Layer by Etching with a HF-containing Solution In Example 1, a bare silicon substrate and a silicon substrate having an oxide ($SiO_2$) layer with a thickness of 1,000 Å were coated with aminosilane and then coated with a photoresist material. Then, both substrates were exposed to UV light through a lithographic mask, developed, and then etched using a HF-containing solution, thereby obtaining the substrates having the patterned surfaces. Autofluorescence signals of the resulting substrates and signals generated from the resulting substrates which were stained with gold/silver or FITC, were measured to estimate the qualities of the formed patterns.

First, the bare silicon substrate and the silicon substrate having the oxide layer with a thickness of 1,000 Å were coated with γ-aminopropyltriethoxysilane (GAPS) using a spin coater (2,000 rpm, 10 sec), and then coated with a positive photoresist material GXR601 (manufactured by Clariant). Then, a mask having a pitch of 1,150 μm and a pattern size of 200 μm×200 μm was arranged on a surface of the photoresist material of each substrate. The substrates were exposed to UV light (365 nm, 13 mW) through the mask using EV 620 Aligner (maximum resolution: 1 μm) and developed using a 1% TMAH developer. Subsequently, the substrates were immersed for 3 minutes in a bath containing a buffered oxide etchant (BOE) ($NH_4F/HF=6/1$) to etch the exposed portion. The remaining photoresist materials were removed using a stripper composed of acetone/isopropyl alcohol/water, thereby obtaining the substrates having the patterned surfaces.

Then, the obtained substrates were stained with gold/silver or FITC and signals generated from the substrates were measured using a scanner (manufactured by Axon). The results are shown in FIG. 1. FIG. 1 illustrates the results of fluorescent measurements at 532 nm for autofluorescence signals of the resulting substrates and signals generated from the resulting substrates, which were stained with gold/silver or FITC, using the scanner (manufactured by Axon). Referring to FIG. 1, it is confirmed that the patterns were formed on the bare silicon substrate and the silicon substrate having the oxide layer with a thickness of 1,000 Å and the pattern formed on the latter appears clearer than the pattern formed on the bare silicon substrate. It is believed that such a clear pattern on the silicon substrate having the oxide layer with a thickness of 1,000 Å occurs because of the presence of the $SiO_2$ layer. That is, it is regarded that in the silicon substrate having the $SiO_2$ layer having a thickness of 1,000 Å, the signal was increased due to the effect of optical constructive interference.

Figure 2:
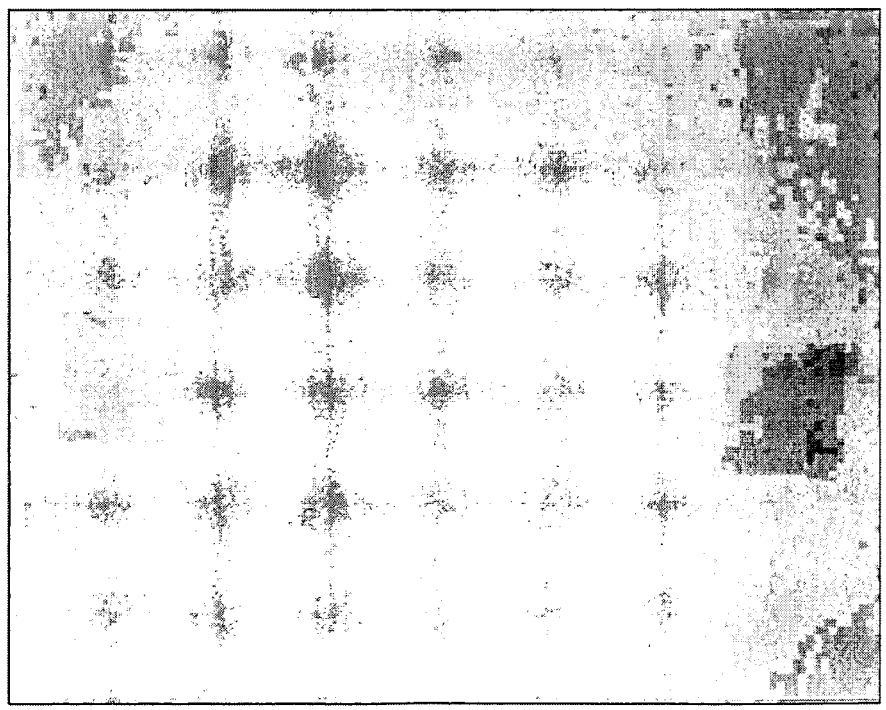
FIG. 2 is a scanning electron microscopic (SEM) photo of a surface of a silicon wafer substrate having a patterned surface produced using a method according to an embodiment of the present invention.

To compensate for a reduction in the fluorescent signal in the bare silicon substrate, the surface of the bare silicon substrate was observed with an electron microscope. FIG. 2 is an electron microscopic photo of a surface of a silicon wafer substrate having a patterned surface. Referring to FIG. 2, it is confirmed that a clear pattern was formed on the substrate.

Example 2

Measurement of Resolution of a Pattern Produced According to a Method Comprising Etching with a HF-containing Solution In Example 2, a bare silicon substrate and a silicon substrate having an oxide ($SiO_2$) layer with a thickness of 1,000 Å were coated with aminosilane and then coated with a photoresist material. Then, they were exposed to UV light through a lithographic mask, developed, and then etched using a HF-containing solution, thereby obtaining the substrates having the patterned surfaces. The surfaces of the resulting substrates were observed with an optical microscope and an atomic force microscope (AFM) to estimate the resolution between the patterns.

First, the bare silicon substrate and the silicon substrate having the oxide layer with a thickness of 1,000 Å were coated with GAPS using a spin coater (2,000 rpm, 10 sec), and then coated with a positive photoresist material GXR601 (manufactured by Clariant). Then, a mask for resolution measurements was positioned on a surface of the photoresist material of each substrate. The substrates were exposed to UV light (365 nm, 13 mW) through the mask using EV 620 Aligner (maximum resolution: 1 µm) and developed using a 1% TMAH developer. Subsequently, the substrates were immersed for 3 minutes in a bath containing a BOE ($NH_4F/HF=6/1$) to etch the exposed portion. The remaining photoresist materials were removed using a stripper composed of acetone/isopropyl alcohol/water, thereby obtaining the substrates having the patterned surfaces.

Figure 3A:
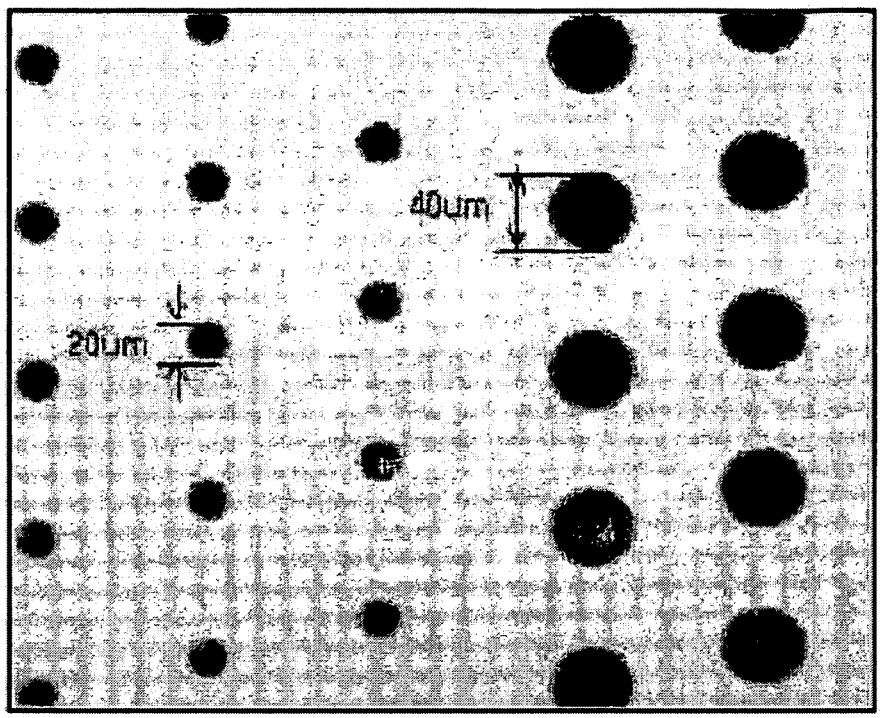
FIGS. 3A through 3C are views illustrating the results of resolutions between patterns formed on a silicon substrate having an oxide layer with a thickness of 1,000 Å, produced using a method according to an embodiment of the present invention, observed using an optical microscope.
Figure 3B:
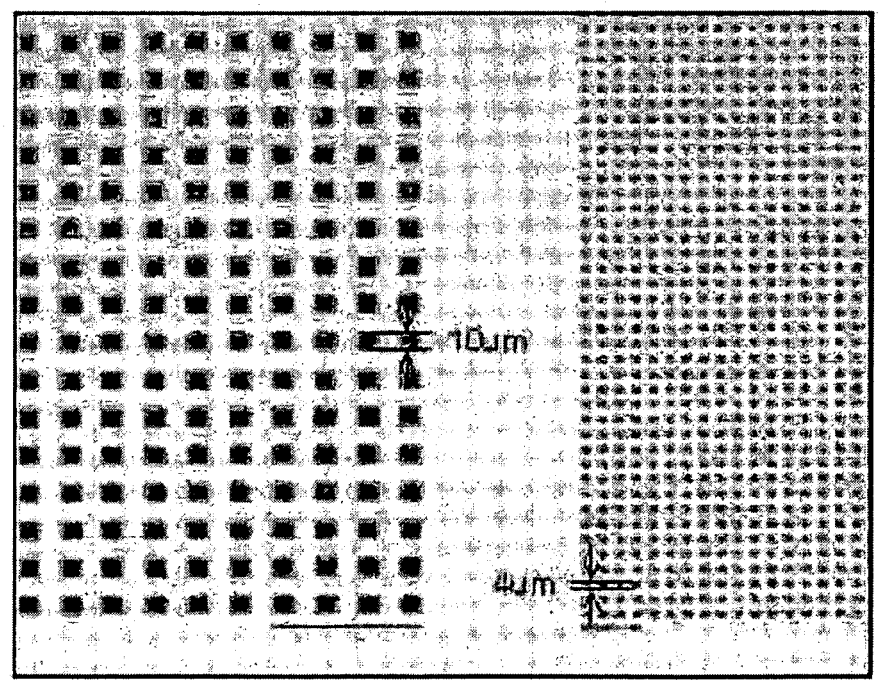
Figure 3C:
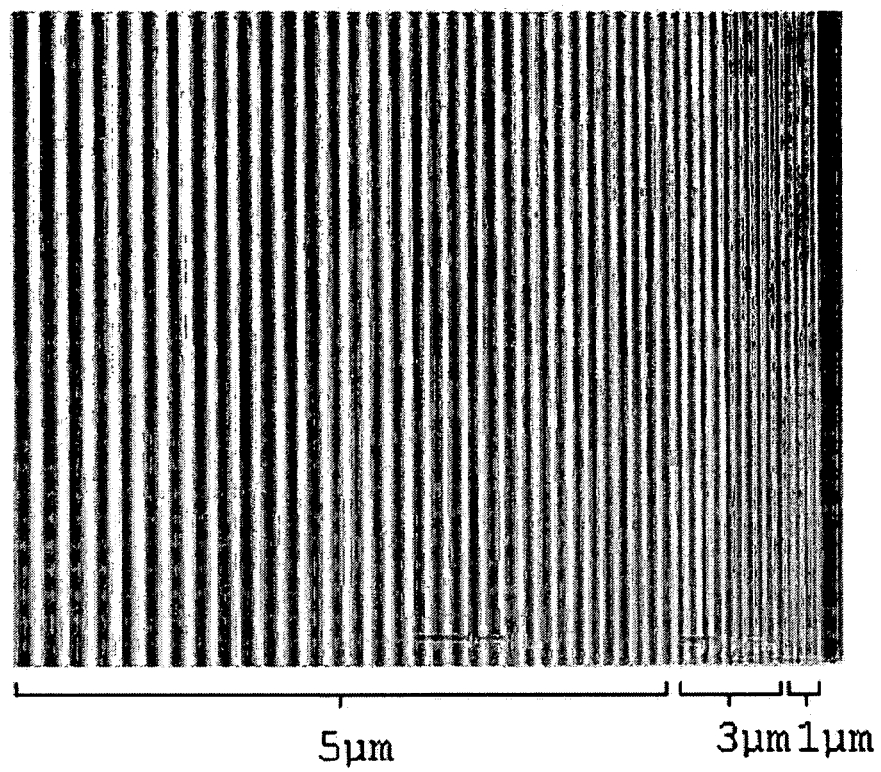
Figure 4:
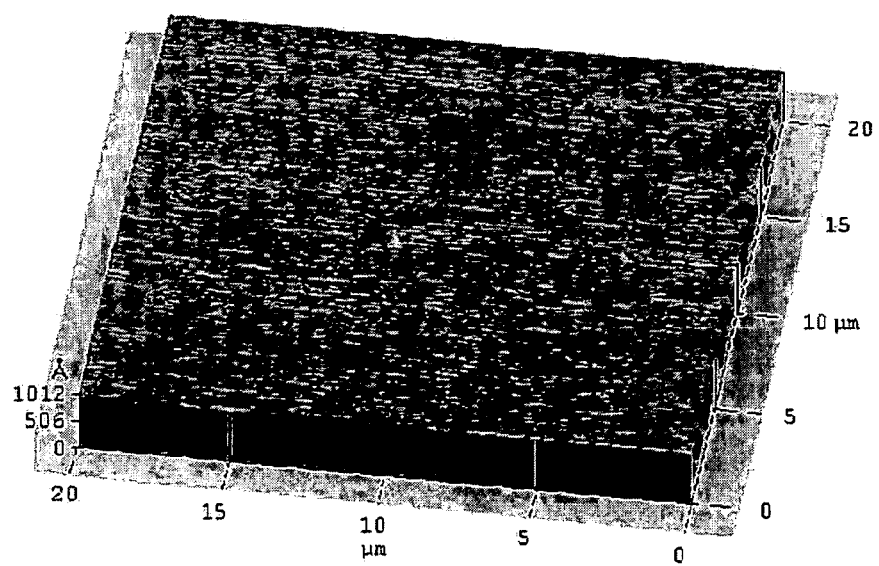
FIG. 4 is a view illustrating the resolution results between patterns formed on a bare silicon substrate produced using a method according to an embodiment of the present invention, observed using an AFM (atomic force microscope)

Then, the obtained substrates were observed with an optical microscope and an AFM to estimate the resolution between the patterns. The results are shown in FIGS. 3A through 3C and 4. FIGS. 3A through 3C illustrate the results of the resolutions between the patterns formed on the silicon substrate having the oxide layer with a thickness of 1,000 Å, observed using an optical microscope. Referring to FIG. 3A, it is possible to obtain a resolution of 20 µm. Referring to FIG. 3B, it is possible to obtain a resolution of 4 µm. Referring to FIG. 3C, it is possible to obtain a resolution of about 1 µm. FIG. 4 is a view illustrating the results of the resolution between the patterns formed on the bare silicon substrate, observed using an AFM. Referring to FIG. 4, it is possible to obtain a resolution of about 2 µm.

Example 3

Copper Plating on the Pattern of the Substrate Produced Using the Method According to an Embodiment of the Present Invention In Example 3, copper plating was performed on the pattern of the substrate produced using the method according to an embodiment of the present invention, and then, the results were observed.

First, a bare silicon substrate was coated with GAPS using a spin coater (2,000 rpm, 10 sec), and then coated with a positive photoresist material GXR601 (manufactured by Clariant). Then, a mask having a pitch of 1,150 µm and a pattern size of 200 µm×200 µm or a mask for resolution measurement was arranged on a surface of the photoresist material of the substrate. The substrate was exposed to UV light (365 nm, 13 mW) through the mask using EV 620 Aligner (maximum resolution: 1 µm) and developed using a 1% TMAH developer. Subsequently, the substrate was immersed for 3 minutes in a bath containing a BOE ($NH_4F/HF=6/1$) to etch the exposed portion. The remaining photoresist material was removed using a stripper composed of acetone/isopropyl alcohol/water, thereby obtaining the substrate having the patterned surface.

Then, the obtained substrate was copper plated (Electrochimica Acta 49: p1613, 2004). First, the patterned silicon substrate was activated by reacting said substrate in a $PdCl_2$ solution (1 g/l) for 1 minute. Then, the activated substrate was copper plated by immersing said substrate in an electroless plating solution for 30 minutes. The electroless plating solution was produced using $CuSO_4$ (0.05M), EDTA (0.055M), formaldehyde (0.15M), and NaOH (adjust pH to 12).

Figure 5A:
FIGS. 5A and 5B are views illustrating the results of patterned surfaces of a bare silicon substrate without copper plating and a copper plated, patterned surface of a bare silicon substrate, respectively, observed using an optical microscope, wherein the patterns were formed using a mask having a pitch of 1,150 µm and a pattern size of 200 µm×200 µm.
Figure 5B:
Figure 6:
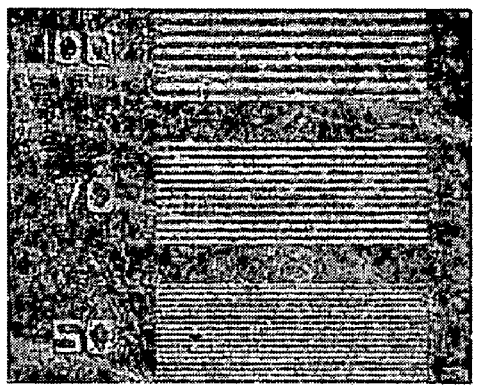
FIG. 6 is a view illustrating a copper plated, patterned surface of a bare silicon substrate, observed using an optical microscope, wherein the pattern was formed using a mask for a resolution measurement.
Figure 6:
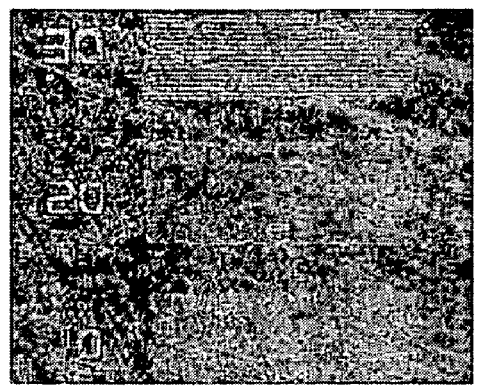

Thus, the substrate having the patterned surface which was copper plated was obtained. FIGS. 5A, 5B and 6 are views illustrating the results of the substrates having copper plated or not on the patterned surface, observed using an optical microscope. FIGS. 5A and 5B are views illustrating the results of the patterned surface of the bare silicon substrate without copper plating and the copper plated, patterned surface of the bare silicon substrate, respectively, observed using an optical microscope, wherein the patterns were formed using the mask having a pitch of 1,150 µm and a pattern size of 200 µm×200 µm. Referring to FIGS. 5A and 5B, it is confirmed that the copper plated, patterned surface was clearer with an optical microscope when compared to the patterned surface of the bare silicon substrate. This shows that by using the substrate having the patterned surface obtained using the method according to an embodiment of the present invention, the surface of the substrate can be selectively metalized. FIG. 6 is a view illustrating the copper plated, patterned surface of the bare silicon substrate, observed using an optical microscope, wherein the pattern was formed using the mask for resolution measurement. Referring to FIG. 6, it is confirmed that it is possible to obtain a resolution of about 30 µm or more.

Example 4

DNA Immobilization on the Pattern of the Substrate Produced Using the Method According to an Embodiment of the Present Invention In Example 4, oligonucleotide was immobilized on the pattern of the substrate produced using the method according to an embodiment of the present invention, and then, the results were observed.

First, a silicon substrate having an oxide layer with a thickness of 1,000 Å was coated with GAPS using a spin coater (2,000 rpm, 10 sec), and then coated with a positive photoresist material GXR601 (manufactured by Clariant).

Then, a mask for a microarray was arranged on a surface of the photoresist material of the substrate. The substrate was exposed to UV light (365 nm, 13 mW) through the mask using EV 620 Aligner (maximum resolution: 1 µm) and developed using a 1% TMAH developer. Subsequently, the substrate was immersed for 3 minutes in a bath containing a BOE (NH$_4$F/HF=6/1) to etch the exposed portion. The remaining photoresist material was removed using a stripper composed of acetone/isopropyl alcohol/water, thereby obtaining the substrate having the patterned surface.

Figure 7:
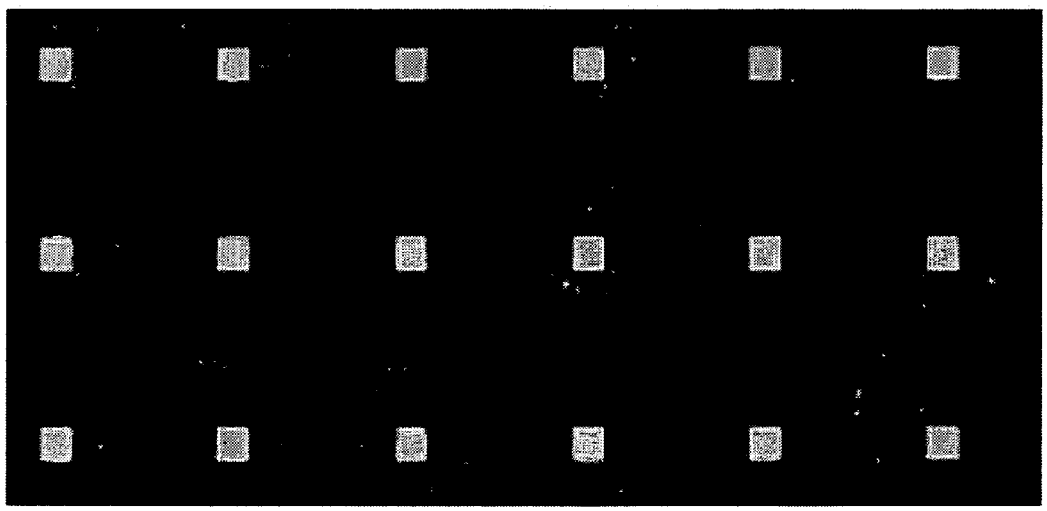
FIG. 7 is a view of hybridization of a target nucleic acid labeled with Cy-3 to an oligonucleotide immobilized on a substrate having a patterned organosilane layer produced

Then, an immobilization mixture containing an oligonucleotide was spotted on the obtained substrate using the Nanodispenser™ (manufactured by Sequonom) for immobilization. The oligonucleotide has a hexamethyleneamino group at its 5' end (SEQ ID No.1). A target nucleic acid labeled with Cy-3 at its 3' end (SEQ ID No.2) was hybridized to the oligonucleotide having SEQ ID No. 1 immobilized on the microarray and their hybridization was determined using a scanner (manufactured by Axon). The results are shown in FIG. 7. FIG. 7 is a view of the hybridization of the target nucleic acid labeled with Cy-3 with the oligonucleotide immobilized on the substrate produced using the method according to an embodiment of the present invention, determined using the scanner. Referring to FIG. 7, it is confirmed that the substrate having the patterned surface produced using the method according to an embodiment of the present invention can be useful in manufacturing an oligonucleotide array.

Since the method of producing the substrate having the patterned organosilane layer comprises etching using the HF-containing solution, the substrate having the patterned organosilane layer can be rapidly produced in a simple manner on a large scale at low costs. The patterned surface of the substrate produced using the method according to the present invention can selectively react the surface of the substrate with a biomolecule, metal, or other materials.

Since the biomolecule array production method of the present invention comprises etching using the HF-containing solution, the biomolecule microarray can be manufactured in a simple manner at low costs.

While the present invention has been particularly shown and described with reference to exemplary embodiments thereof, it will be understood by those of ordinary skill in the art that various changes in form and details may be made therein without departing from the spirit and scope of the present invention as defined by the following claims.

---

---

What is claimed is:

1. A method of producing a substrate having a patterned organosilane layer, comprising:
   coating organosilane directly on a substrate to obtain an organosilane layer,
   wherein the substrate is made of a material selected from the group consisting of silicon, glass, silica, diamond, quartz, alumina, platinum, gold, aluminum, tungsten, titanium, polyester, polyamide, polyimide, polyether, polysulfone, and fluoropolymer,
   wherein the organosilane is selected from the group consisting of aminosilane, epoxysilane, and fluorosilane;
   coating a photoresist material on the organosilane layer;
   exposing the photoresist material to light through a mask to obtain a patterned surface on the photoresist material;
   developing an exposed or unexposed region of the photoresist material using a developer; and
   wet etching a portion of the organosilane layer in the region from which the photoresist material has been removed, using a HF-containing solution as an etchant.

2. The method of claim 1, wherein the amino silane is γ-aminopropyltriethoxysilane (GAPS) or N-(2-aminoethyl)-3-aminopropyltrimethoxysilane.

3. The method of claim 1, wherein the epoxysilane is (3-glycidoxypropy)trimethoxysilane or 2-(3,4-epoxycyclohexyl)ethyltrimethoxysilane.

4. The method of claim 1, wherein the fluorosilane is 1H,1H,2H,2H-perfluorodecyltriethoxysilane.

5. The method of claim 1, wherein the substrate is able to be modified to have a hydroxyl group on its surface.

6. The method of claim 5, wherein the substrate has a layer of $SiO_2$, $Al_2O_3$, $TiO_2$, or ITO on its surface.

7. The method of claim 6, wherein when the organosilane layer is coated on the substrate having a layer of $SiO_2$ on its surface, the portions of the organosilane layer and the $SiO_2$ layer in the region from which the photoresist material has been removed are simultaneously wet etched using the HF-containing solution as an etchant.

8. The method of claim 1, wherein the HF-containing solution is a HF solution, a buffered HF solution, or a solution containing HF as a primary component.

* * * * *